United States Patent [19]

Wilk et al.

[11] Patent Number: 5,240,675
[45] Date of Patent: Aug. 31, 1993

[54] METHOD FOR CLEANING ENDOSCOPE

[76] Inventors: Peter J. Wilk, 185 West End Ave., New York, N.Y. 10023; Jonathan Tiefenbrun, 62 Country Rd., Mamaroneck, N.Y. 10543

[21] Appl. No.: 950,818

[22] Filed: Sep. 24, 1992

[51] Int. Cl.⁵ .......................... A61L 2/08; B08B 9/00
[52] U.S. Cl. ........................................ 422/22; 422/20; 422/24; 422/292; 422/294; 219/10.55 R; 250/455.11; 15/104.2; 15/104.05; 604/265; 606/15; 606/29; 606/33
[58] Field of Search ............... 422/20, 24, 22, 294, 422/307, 28, 292, 905, 907; 604/21, 265, 266, 267; 128/786; 219/10.55 R; 220/87.1; 250/455.11; 606/15, 29, 33; 15/104.2, 104.05

[56] References Cited

U.S. PATENT DOCUMENTS 5,061,255 10/1991 Greenfeld et al. ............ 604/265 X
5,168,593 12/1992 Poje et al. ........................ 15/104.2

OTHER PUBLICATIONS

"Endoscopic Contamination and Disinfection Annotated Bibliography", by David H. Spach, M.D., University of Wash., Seattle, Washington, May 1992, pp. 1-28.

Primary Examiner—Robert J. Warden
Assistant Examiner—E. Leigh Dawson
Attorney, Agent, or Firm—R. Neil Sudol; Henry D. Coleman

[57] ABSTRACT

In a method for use in cleaning a flexible endoscope, an elongate cleaning member having an embedded optical fiber, an electrical conductor, and/or a heat conductor is inserted into a biopsy channel of the endoscope. Sterilizing radiation of a predetermined wavelength is transmitted along the optical fiber from a proximal end of the elongate cleaning member towards a distal end thereof. The radiation is dispersed to at least partially sterilize the biopsy channel. Heat energy is conducted along the heat conductor to raise or lower the temperature of the biopsy channel for a predetermined period to effectuate a sterilizing action. Electrical current may also be transmitted along the biopsy channel wall by virtue of the electrical conductor. The method also comprises the step of ejecting a sterilizing fluid from the elongate cleaning member into the biopsy channel. Where a brush or friction element is provided at the distal end of the elongate cleaning member, the brush or friction element is used to scrub the biopsy channel with the sterilizing fluid. The scrubbing may be implemented by vibrating the elongate cleaning member, e.g., by transmitting an ultrasonic wave through the elongate cleaning member.

28 Claims, 2 Drawing Sheets

METHOD FOR CLEANING ENDOSCOPE

BACKGROUND OF THE INVENTION

This invention relates to a method for cleaning an endoscope. More particularly, this invention relates to a method for cleaning the biopsy channel of a flexible endoscope.

Endoscopes are medical instruments which enable a relatively non-intrusive visual inspection of and surgery on internal body tissues, particularly body tissues located within the digestive tract. An endoscope includes a long flexible tubular member which is inserted into the colon through the anus or into the esophagus through the mouth or the nose.

The tubular insertion member of an endoscope generally includes optical fibers for carrying light energy into the patient and for carrying organized visual information out of the patient. The insertion member also includes an elongate cylindrical channel ("biopsy channel") for inserting a surgical instrument into the patient.

The operating tip of a surgical instrument which is inserted through the ancillary, biopsy, channel of an endoscope is controlled by a surgeon who manipulates an actuator at the proximal end of the endoscope. The operation is visually monitored via the visual feedback information provided by the endoscope. Larger endoscopes, particularly for use in the colon, may contain several ancillary channels, e.g., for applying suction and for feeding water and/or air to the distal end of the endoscope's insertion member.

Because endoscopes are expensive instruments, they are used on multiple patients and must accordingly be sterilized after each procedure. Sterilization generally entails soaking at least the distal end of the endoscope's insertion member in a antibacterial and antiviral solution. In addition, the operating channels of the insertion member must be flushed, preferably with a sterilizing solution.

Such sterilization procedures require substantial amounts of time. Costs are increased, not only because of the hospital personnel time involved, but also because the endoscopes are out of use for that additional time.

Moreover, there is always the risk that sterilization is inadequate and that renegade bacteria or viruses remain in the endoscope, particularly in the biopsy channel, and may be subsequently transferred to a patient. This risk cannot be ignored in the present environment of AIDS and other dreaded diseases.

OBJECTS OF THE INVENTION

An object of the present invention is to provide a method for facilitating sterile endoscopic surgery.

Another object of the present invention is to provide such a method which enhances the sterilization of endoscopes.

A more particular object of the present invention is to provide such a method which facilitates cleaning or sterilization of the biopsy channel of an endoscope.

Another, more particular, object of the present invention is to provide such a device and related method which are easy to use.

These and other objects of the present invention will be apparent from the drawings and detailed descriptions herein.

SUMMARY OF THE INVENTION

A method for use in cleaning a flexible endoscope, comprises, in accordance with the present invention, the steps of (a) providing an elongate cleaning member having an optical fiber extending longitudinally through at least a distal end portion of the elongate cleaning member, (b) inserting the distal end portion of the elongate cleaning member into a biopsy channel of the endoscope, (c) transmitting sterilizing radiation of a predetermined wavelength along the optical fiber from a proximal end of the distal end portion towards a distal end of the elongate cleaning member while the distal end portion of the elongate cleaning member is inserted into the biopsy channel, and (d) dispersing transmitted sterilizing radiation from the optical fiber to at least partially sterilize the biopsy channel.

According to another feature of the present invention, the method also comprises the step of ejecting a sterilizing fluid from the elongate cleaning member into the biopsy channel. Where a brush or friction element is provided at the distal end of the elongate cleaning member, the method additionally comprising the step of using the brush or friction element to scrub the biopsy channel with the sterilizing fluid. The scrubbing may be implemented by vibrating the elongate cleaning member, e.g., by transmitting an ultrasonic wave through the elongate cleaning member.

According to a further feature of the present invention, the method includes the step of moving the elongate cleaning member through the biopsy channel during the transmission and dispersion of the sterilizing radiation.

According to a specific embodiment of the present invention, the optical fiber is one of a plurality of optical fibers extending along the segment of the catheter, the sterilizing radiation being transmitted through all of the fibers.

The sterilizing radiation may be in the ultraviolet or infrared portion of the electromagnetic spectrum.

A method for use in cleaning a flexible endoscope comprises, in accordance with another embodiment of the present invention, the steps of (i) providing an elongate cleaning member having a heat conductor extending longitudinally through at least a distal end portion of the elongate cleaning member, (ii) inserting the distal end portion of the elongate cleaning member into a biopsy channel of the endoscope, and (iii) upon insertion of the distal end portion of the elongate cleaning member into the biopsy channel, transferring heat energy between the biopsy channel and the heat conductor to provide the biopsy channel with a predetermined temperature for a predetermined period of time.

This embodiment of the invention may also include the additional step of ejecting a sterilizing fluid from the elongate cleaning member into the biopsy channel. As described hereinabove, where a brush or friction element is provided at the distal end of the elongate cleaning member, the method additionally comprising the step of using the brush or friction element to scrub the biopsy channel with the sterilizing fluid. The scrubbing may be implemented by vibrating the elongate cleaning member, e.g., by transmitting an ultrasonic wave through the elongate cleaning member.

Pursuant to another feature of the present invention, this embodiment of the invention also includes the step of connecting the conductor at a proximal end of the elongate cleaning member to an external heat exchanger.

The predetermined temperature may be an elevated temperature, in which case heat energy is transfered from the conductor to the biopsy channel. Alternatively, the predetermined temperature may be a lowered temperature, in which case heat energy is transfered to the conductor from the biopsy channel.

A method for use in cleaning a flexible endoscope comprises, in accordance with a further embodiment of the present invention, the steps of (1) providing an elongate cleaning member having an electrical conductor extending longitudinally through at least a distal end portion of the elongate cleaning member, (2) inserting the distal end portion of the elongate cleaning member into a biopsy channel of the endoscope, (3) upon insertion of the distal end portion of the elongate cleaning member into the biopsy channel, conducting electrical current through the conductor, and (4) using the electrical current to at least partially sterilize the biopsy channel along the distal end portion of the elongate cleaning member.

This embodiment of the invention may also include the additional step of ejecting a sterilizing fluid from the elongate cleaning member into the biopsy channel. As described hereinabove, where a brush or friction element is provided at the distal end of the elongate cleaning member, the method additionally comprising the step of using the brush or friction element to scrub the biopsy channel with the sterilizing fluid. The scrubbing may be implemented by vibrating the elongate cleaning member, e.g., by transmitting an ultrasonic wave through the elongate cleaning member.

In accordance with another feature of the present invention, electrical current from the electrical conductor is converted into heat energy which is then transfered to the biopsy channel to elevate the temperature of the biopsy channel for a predetermined period of time.

In accordance with yet another feature of the present invention, the conductor is one of a pair of electrical conductors connected to respective terminals spaced from one another along the elongate cleaning member. To sterilize the biopsy channel, electrical current is conducted along a wall of the biopsy channel between the terminals or contacts.

A method in accordance with the present invention facilitates sterile endoscopic surgery by enhancing the sterilization process. Bacteria, fungus and viruses in the biopsy channel of an endoscope may be attacked with a multiplicity of biocidal techniques to eliminate the undesirable microorganisms from along the length of the biopsy channel.

DETAILED DESCRIPTION

Figure 1:
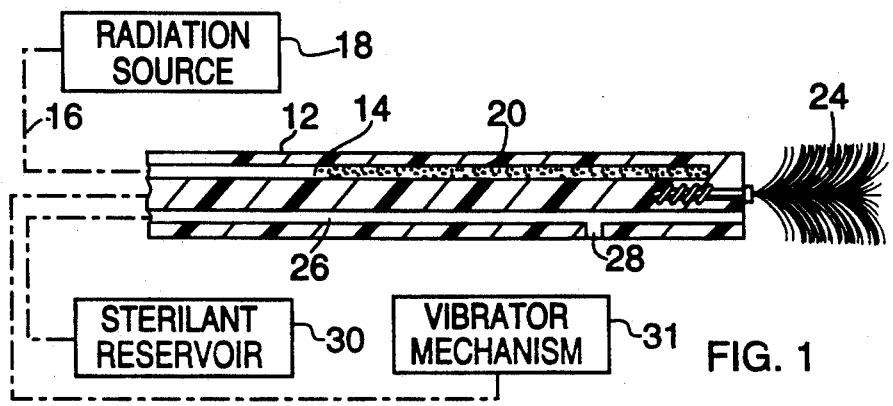
FIG. 1 is partially a partial longitudinal cross-sectional view, on an enlarged scale, and partially a block diagram of an assembly for use in cleaning a biopsy channel in a method accordance with the present invention.

As illustrated in FIG. 1, an assembly for use in cleaning a biopsy channel of an endoscope, particularly a flexible endoscope, comprises a flexible elongate cleaning member 12 insertable into the endoscope biopsy channel and at least one optical fiber 14 embedded in the elongate cleaning member and extending longitudinally along at least a segment of the elongate cleaning member. Optical fiber 14 transmits electromagnetic radiation within a predetermined range of wavelengths, for example, in the ultraviolet or infrared portions of the spectrum and is coupled at a proximal end via a schematically represented connector 16 to a source 18 of ultraviolet or infrared radiation.

The radiation produced by source 18 and carried by fiber 14 includes radiation of a wavelength which is predetermined to be effective in inhibiting growth of a selected kind of microorganism, for example, a bacterium which is characteristically found in endoscope biopsy channels upon completion of an endoscopic diagnostic procedure or treatment.

Along a terminal segment 20, fiber 14 is provided with a roughened surface which disperses incoming radiation of the predetermined frequency generated by source 18. In some application, it may be desirable to provide a plurality of optical fibers 14 each carrying a respective sterilizing wavelength. (See FIG. 5.) Alternatively, the different fibers may all be connected to the same source 18. In either case, the different fibers may extend different distances and accordingly terminate at different points along elongate cleaning member 12.

Generally, it is contemplated that elongate cleaning member 12 is inserted into the biopsy channel of an endoscope so that a brush 24 mounted to the distal end of elongate cleaning member 12 protrudes from the distal end of the biopsy channel and so that roughened terminal segment 20 of fiber 14 is coextensive with the terminal or distal end portion of the biopsy channel. Cleaning member 12 is then pulled back through the endoscope biopsy channel at a rate sufficient to ensure effective sterilization by the radiation by terminal segment 20.

The cleaning assembly of FIG. 1 additionally comprises a channel or bore 26 which extends longitudinally through elongate cleaning member 12 and which is provided at a distal end with one or more openings 28. At a proximal end, channel or bore 26 is connected to a pressurized or pressurizable sterilant reservoir 30. During use of the cleaning assembly of FIG. 1, liquid sterilant is pumped or forced from reservoir 30 through channel 26 and out through openings 28. Brush 24 scrubs the sterilant into the inner walls of the endoscope biopsy channel.

To facilitate the action of brush 24, elongate cleaning member 12 is coupled at a proximal end to a vibrator mechanism 31 for imparting an oscillating or reciprocating motion to brush 24 during a pushing or pulling of cleaning member 12 through an endoscopic biopsy channel. The vibration frequency imparted by mechanism 31 may be of any suitable magnitude, such as ultrasonic.

Figure 2:
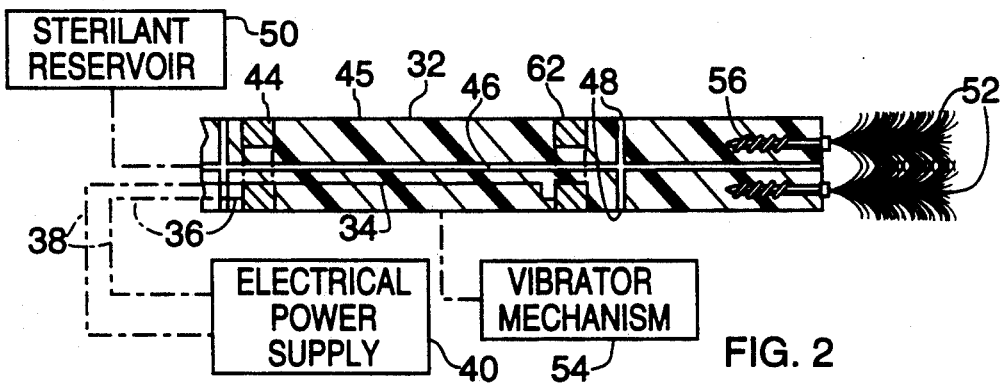
FIG. 2 is partially a partial longitudinal cross-sectional view, on an enlarged scale, and partially a block diagram of another assembly for use in cleaning a biopsy channel in a method accordance with the present invention.

As shown in FIG. 2, another biopsy channel cleaning assembly comprises an elongate cleaning member 32 traversed longitudinally by a pair of embedded annular electrical conductors 34 and 36. A schematically represented connector 38 serves to link conductors 34 and 36 at an input end to a source or supply 40 of electrical power. Elongate cleaning member 32 is provided with sterilization components in the form of two annular terminals or contacts 42 and 44 connected to respective conductors 34 and 36 and embedded in elongate cleaning member 32. Terminals 42 and 44 are disposed along an outer surface 45 of elongate cleaning member 32.

Upon insertion of elongate cleaning member 32 into a biopsy channel of an endoscope, energization of conductors or leads 34 and 36 by supply 40 induces electrical current to flow through residual fluid contained in the biopsy channel after an endoscopic procedure. The electrical current serves to at least incapacitate microorganisms harbored in the biopsy channel.

As discussed hereinabove with reference to FIG. 1, the cleaning assembly of FIG. 2 also includes a channel or bore 46 which extends longitudinally through elongate cleaning member 32 and which is provided at a distal end with one or more openings 48. At a proximal end, channel or bore 46 is connected to a pressurized or pressurizable sterilant reservoir 50. During use of the cleaning assembly of FIG. 2, liquid sterilant is pumped or forced from reservoir 50 through channel 46 and out through openings 48. A plurality of brushes 52 mounted to the distal end of elongate cleaning member 32 serve to scrub the cylindrical wall of the endoscopic biopsy channel. Brushes 52 also serve to spread the liquid disinfectant or sterilant from reservoir 50 along the wall of the endoscope biopsy channel.

To facilitate the action of brushes 52, elongate cleaning member 32 is coupled at a proximal end to a vibrator mechanism 54 which oscillates or reciprocates elongate cleaning member 32 and concomitantly brushes 52 during either a distally or a proximally directed motion of the elongate cleaning member through a biopsy channel of an endoscope. The vibration is preferably at a high frequency, for example, an ultrasonic frequency.

The injection of liquid disinfectant, particularly an ion-containing disinfectant, into an endoscopic biopsy channel during a cleaning operation also has the result of facilitating the sterilization of the biopsy channel by the electrical current transmitted between electrical conductors 34 and 36. Electrical current may be continuously supplied to conductors 34 and 36 from supply 40 during the time that elongate cleaning member 32 is inserted into an endoscope's biopsy channel.

Brushes 52, like brush 24, are provided with flanges spikes or screws 56 for anchoring the brushes in elongate cleaning member 32.

Figure 3:
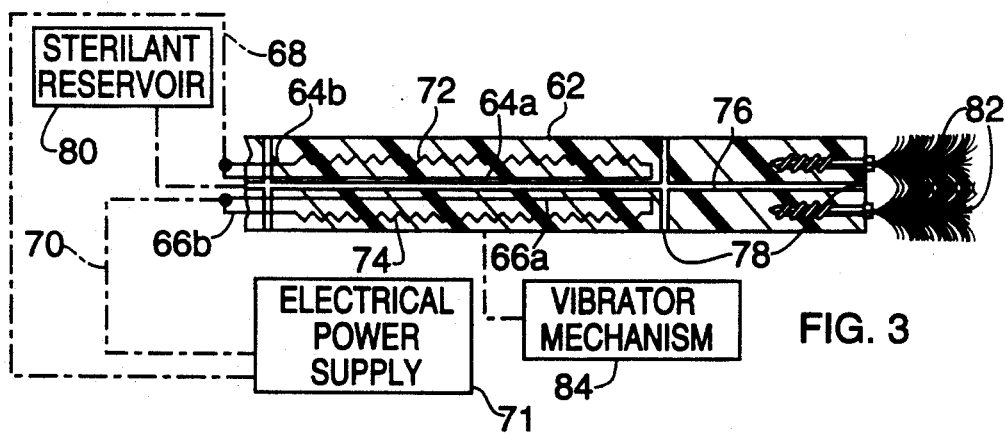
FIG. 3 is partially a partial longitudinal cross-sectional view, on an enlarged scale, and partially a block diagram of a further assembly for use in cleaning a biopsy channel in a method accordance with the present invention.

As depicted in FIG. 3, yet another assembly for use in cleaning an endoscope biopsy channel after an endoscopic procedure comprises a flexible elongate cleaning member 62 traversed longitudinally by two pairs of embedded electrical conductors 64a, 64b and 66a, 66b. Schematically represented connectors 68 and 70 serve to link conductors 64a, 64b and 66a, 66b at input ends to a voltage source or power supply 71. Elongate cleaning member 62 is provided with sterilization components in the form of a plurality of schematically represented resistive heat-generating elements 72 and 74 embedded in a portion of elongate cleaning member 62 for increasing the temperature of that portion relative to an ambient temperature level.

As discussed hereinabove with reference to FIG. 1, the cleaning assembly of FIG. 3 also includes a channel or bore 76 which extends longitudinally through elongate cleaning member 62 and which is provided at a distal end with one or more openings 78. At a proximal end, channel or bore 76 is connected to a pressurized or pressurizable sterilant reservoir 80. During use of the cleaning assembly of FIG. 3, liquid sterilant is pumped or forced from reservoir 80 through channel 76 and out through openings 78. A plurality of brushes 82 mounted to the distal end of elongate cleaning member 62 serve to scrub the cylindrical wall of the endoscopic biopsy channel. Brushes 82 also serve to spread the liquid disinfectant or sterilant from reservoir 80 along the wall of the endoscope biopsy channel.

To facilitate the action of brushes 82, elongate cleaning member 62 is coupled at a proximal end to a vibrator mechanism 84 which oscillates or reciprocates elongate cleaning member 62 and concomitantly brushes 82 during either a distally or a proximally directed motion of the elongate cleaning member through a biopsy channel of an endoscope. The vibration is preferably at a high frequency, for example, an ultrasonic frequency.

Figure 4:
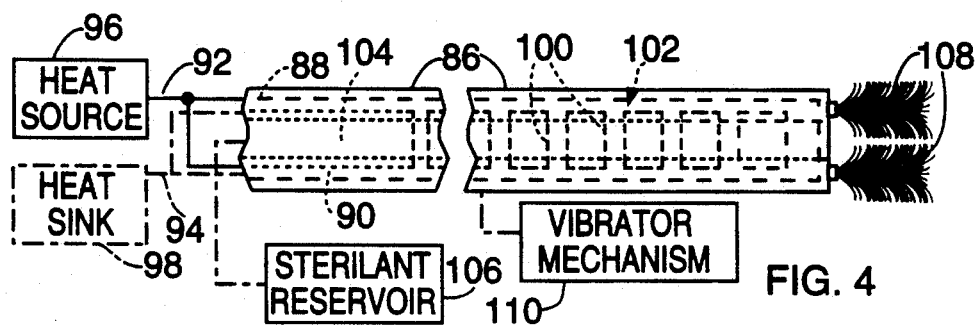
FIG. 4 is partially a partial longitudinal cross-sectional view, on an enlarged scale, and partially a block diagram of yet another assembly for use in cleaning a biopsy channel in a method accordance with the present invention.

A biopsy channel cleaning assembly as shown in FIG. 4 comprises an elongate cleaning member 86 insertable into the biopsy channel of an endoscope, one or more heat conductive conductors 88 and 90 connected to elongate cleaning member 86 and embedded longitudinally in at least a segment of the elongate cleaning member. A schematically illustrated connector 92 or 94 serves to connect conductors 88 and 90 at a proximal or input end to an external heat exchanger in the form of a heat source 96 or, alternatively, a heat sink 98. Conductors 88 and 90 are provided at a distal end with a plurality of annular webs 100 which serve as heating or cooling fins of a heat exchanger 102 at the distal end of conductors 88 and 90.

It is to be noted that a plurality of heat exchange components such as heat exchanger 102 may be provided along the length of elongate cleaning member 86, each such heat exchanger being serviced by a respective heat conductive rod or a plurality of such heat conductors.

Accordingly, conductors 88 and 90 are disposed in such relation to elongate cleaning member 86 (via heat exchanger 102) that heat is exchanged between conductors 88 and 90 and elongate cleaning member 86 along the portion of an endoscope biopsy channel to be sterilized. The direction of heat conduction is into the biopsy channel from the conductos 88 and 90 in elongate cleaning member 86 in the event that heat source 96 is connected to heat exchanger 102 via conductors or rods 88 and 90. Alternatively, the direction of heat conduction is out of the biopsy channel and into elongate cleaning member 86 in the event that conductors 88 and 90 are connected at their proximal ends to heat sink 98.

The amount of heat energy transfered between elongate cleaning member 86 and the endoscope biopsy channel along a predetermined portion thereof changes a temperature of the biopsy channel to a magnitude adapted to at least incapacitate microorganisms of a predetermined variety.

As discussed hereinabove with reference to FIGS. 1-3, elongate cleaning member 86 of FIG. 4 includes a channel or bore 104 connected to a pressurized or pressurizable sterilant reservoir 106. A plurality of brushes 108 are mounted to the distal end of elongate cleaning member 86. Elongate cleaning member 86 is coupled at a proximal end to a vibrator mechanism 110 which oscillates or reciprocates elongate cleaning member 86 and concomitantlly brushes 108 during either a distally or a proximally directed motion of the elongate cleaning member through a biopsy channel of an endoscope.

Figure 5:
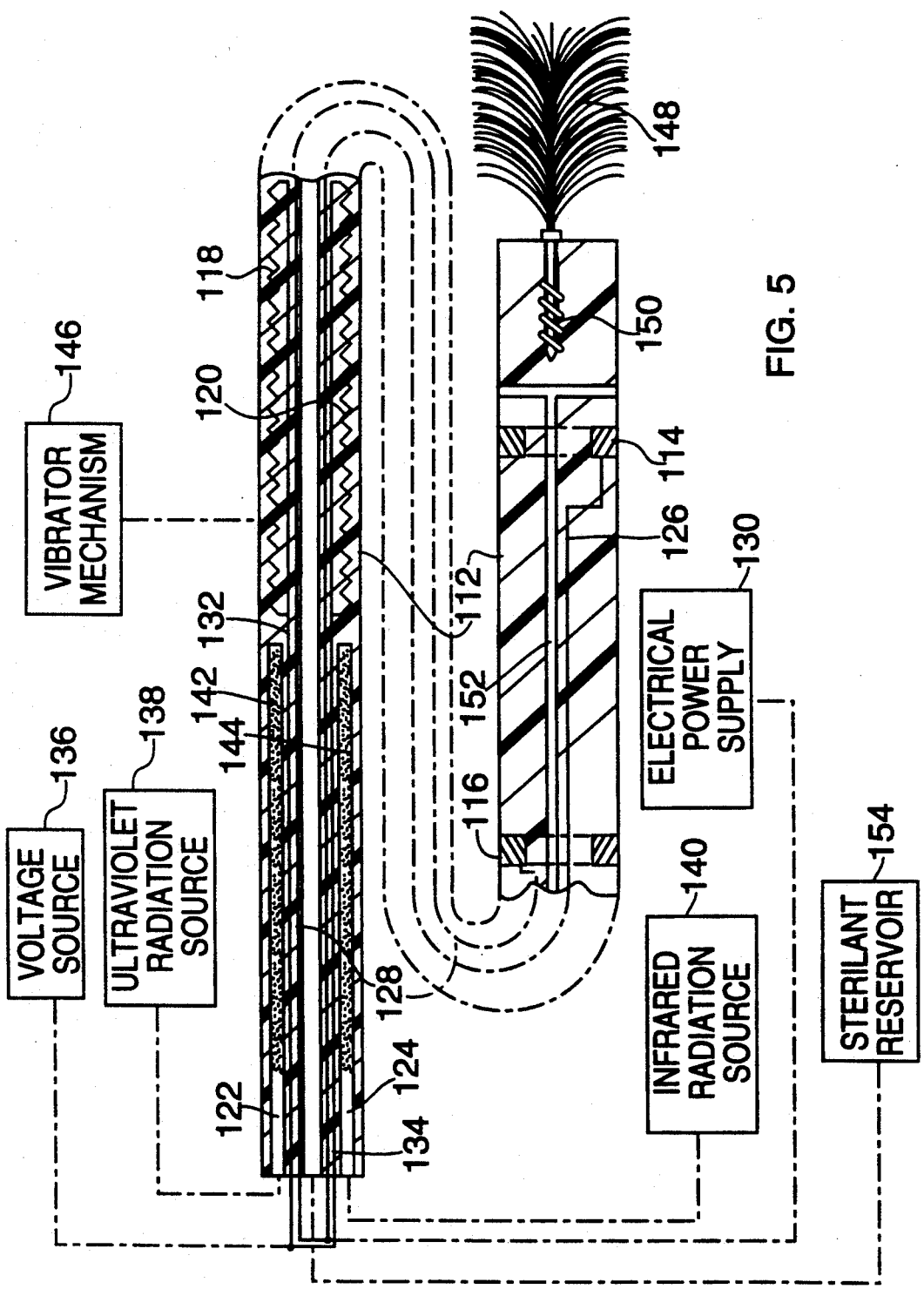
FIG. 5 is partially a partial longitudinal cross-sectional view, on an enlarged scale, and partially a block diagram of an additional assembly for use in cleaning a biopsy channel in a method accordance with the present invention.

FIG. 5 depicts a composite cleaning assembly wherein an elongate cleaning member 112 includes a pair of spaced annular electrical contacts or terminals 114 and 116, a plurality of electrical resistance elements 118 and 120 and a pair of optical fibers 122 and 124. Terminals 114 and 116 are connected via respective electrical leads 126 and 128 to an electrical power supply 130. Electrical resistance elements 118 and 120 are coupled via electrical conductors 132 and 134 to a voltage or current source 136, while optical fibers 122 and 124 extend from an ultraviolet radiation source 138 and an infrared radiation source 140, respectively. Optical fibers 122 and 124 have terminal segments 142 and 144 which are roughened to effectuate a generally radial dispersion of sterilizing radiation. A mechanism 146 is connected to a proximal end of elongate cleaning member 112 for imparting a high-frequency vibratory motion to the elongate cleaning member and concomitantly to a brush 148 connected via a spike or screw 150 to the distal end of the elongate cleaning member 112. A channel 152 extends longitudinally through elongate cleaning member 112 for the dispensing of a liquid disinfectant or sterilizing composition or compound from a reservoir 154.

Although the invention has been described in terms of particular embodiments and applications, one of ordinary skill in the art, in light of this teaching, can generate additional embodiments and modifications without departing from the spirit of or exceeding the scope of the claimed invention. For example, it is possible to sterilize the biopsy channel of an endoscope in a method in accordance with the present invention wherein the distal end of an elongate cleaning member is not provided with a brush. Alternatively, the brushes described and illustrated herein have equivalent forms well within the designing skill of the art. Such alternative brushes may take the form of sponges, pads and other friction elements.

The electrical, thermal, chemical, mechanical, and electromagnetic (radiation) sterilizing functions disclosed herein may be used in different combinations to adequately sterilize and disinfect the biopsy channel of an endoscope. FIG. 5 illustrates but one possible combination.

Accordingly, it is to be understood that the drawings and descriptions herein are proffered by way of example to facilitate comprehension of the invention and should not be construed to limit the scope thereof.

What is claimed is:

1. A method for use in cleaning a flexible endoscope, comprising the steps of:
   providing an endoscope having a flexible insertion member formed with a biopsy channel;
   providing an elongate member having an optical fiber extending longitudinally through at least a distal end portion of said elongate member;
   inserting said distal end portion of said elongate member into said biopsy channel;
   upon insertion of said distal end portion of said elongate member into said biopsy channel, transmitting sterilization radiation of a predetermined wavelength along said optical fiber from a proximal end of said distal end portion towards a distal end of said elongate member; and
   dispersing transmitted sterilizing radiation at least partially radially outwardly from said optical fiber and said elongate member to at least partially sterilize said biopsy channel.

2. The method defined in claim 1, further comprising the step of ejecting a sterilizing fluid from said elongate member into said biopsy channel.

3. The method defined in claim 2 wherein said elongate member is provided at a distal end with a brush element, further comprising the step of using said brush element to scrub said biopsy channel with said sterilizing fluid.

4. The method defined in claim 3, further comprising the step of vibrating said elongate member to enhance the scrubbing of said biopsy channel.

5. The method defined in claim 4 wherein said step of vibrating includes the step of transmitting an ultrasonic wave through said elongate member.

6. The method defined in claim 1, further comprising the step of moving said elongate member through said biopsy channel during said steps of transmitting and dispersing.

7. The method defined in claim 1 wherein said optical fiber is one of a plurality of optical fibers extending along said segment of said catheter, said sterilizing radiation being transmitted through all of said fibers.

8. The method defined in claim 1 wherein said sterilizing radiation is in the ultraviolet portion of the electromagnetic spectrum.

9. The method defined in claim 1 wherein said sterilizing radiation is in the infrared portion of the electromagnetic spectrum.

10. A method for use in cleaning a flexible endoscope, comprising the steps of:
    providing an endoscope having a flexible insertion member formed with a biopsy channel;
    providing an elongate member having a heat conductor extending longitudinally through at least a distal end portion of said elongate member;
    inserting said distal end portion of said elongate member into said biopsy channel; and
    upon insertion of said distal end portion of said elongate member into said biopsy channel, transferring heat energy between said biopsy channel and said heat conductor to provide said biopsy channel with a predetermined temperature for a predetermined period of time.

11. The method defined in claim 10, further comprising the step of ejecting a sterilizing fluid from said elongate member into said biopsy channel.

12. The method defined in claim 11 wherein said elongate member is provided at a distal end with a brush element, further comprising the step of using said brush element to scrub said biopsy channel with said sterilizing fluid.

13. The method defined in claim 12, further comprising the step of vibrating said elongate member to enhance the scrubbing of said biopsy channel.

14. The method defined in claim 13 wherein said step of vibrating includes the step of transmitting an ultrasonic wave through said elongate member.

15. The method defined in claim 10, further comprising the step of connecting said conductor at a proximal end of said elongate member to an external heat exchanger.

16. The device defined in claim 10 wherein said predetermined temperature is a temperature sufficiently elevated to eliminate undesirable microorganisms, said step of transferring including the step of transferring heat energy from said conductor to said biopsy channel.

17. The device defined in claim 10 wherein said predetermined temperature is a temperature sufficiently low to eliminate undesirable micro-organisms, said step of transferring including the step of transferring heat energy from said conductor from said biopsy channel.

18. A method for use in cleaning a flexible endoscope, comprising the steps of:
   providing an endoscope having a flexible insertion member formed with a biopsy channel;
   providing an elongate member having an electrical conductor extending longitudinally through at least a distal end portion of said elongate member;
   inserting said distal end portion of said elongate member into said biopsy channel;
   upon insertion of said distal end portion of said elongate member into said biopsy channel, conducting electrical current through said conductor; and
   additionally conducting said electrical current from said conductor and outwardly of said elongate member to a least partially sterilize said biopsy channel along said distal end portion of said elongate member.

19. The method defined in claim 18, further comprising the step of ejecting a sterilizing fluid from said elongate member into said biopsy channel.

20. The method defined in claim 19 wherein said elongate member is provided at a distal end with a brush element, further comprising the step of using said brush element to scrub said biopsy channel with said sterilizing fluid.

21. The method defined in claim 20, further comprising the step of vibrating said elongate member to enhance the scrubbing of said biopsy channel.

22. The method defined in claim 21 wherein said step of vibrating includes the step of transmitting an ultrasonic wave through said elongate member.

23. A method for use in cleaning a flexible endoscope, comprising the steps of:
   providing an endoscope having a flexible insertion member formed with a biopsy channel;
   providing an elongate member having an electrical conductor extending longitudinally through at least a distal end portion of said elongate member;
   inserting said distal end portion of said elongate member into said biopsy channel;
   upon insertion of said distal end portion of said elongate member into said biopsy channel, conducting electrical current through said conductor; and
   converting said electrical current into heat energy and transferring said heat energy to said biopsy channel from said conductor to elevate the temperature of said biopsy channel for a predetermined period of time sufficient to eliminate undesirable microorganisms in said biopsy channel.

24. The method defined in claim 18 wherein said conductor is one of a pair of conductors connected to respective terminals spaced from one another along said elongate member, said step of using including the step of conducting electrical current along a wall of said biopsy channel between said terminals.

25. A method for use in cleaning a flexible endoscope, comprising the steps of:
   providing an endoscope having a flexible insertion member formed with a biopsy channel;
   providing an elongate tubular member having a friction element and an aperture at a distal end;
   inserting a distal end portion of said elongate tubular member into said biopsy channel;
   ejecting a sterilizing fluid from said tubular member through said opening into said biopsy channel;
   using said friction element to scrub said biopsy channel with said sterilizing fluid; and
   ultrasonically vibrating said friction member to enhance the scrubbing of said biopsy channel.

26. The method defined in claim 25, further comprising the steps of:
   transmitting sterilizing radiation of a predetermined wavelength along an optical fiber in said tubular member from a proximal end of said distal end portion towards said distal end of said tubular member while said distal end portion of said tubular member is inserted into said biopsy channel; and
   dispersing transmitted sterilizing radiation from said optical fiber to at least partially sterilize said biopsy channel.

27. The method defined in claim 25, further comprising the step of, upon insertion of said distal end portion of said tubular member into said biopsy channel, transferring heat energy between said biopsy channel and a heat conductor in said tubular member to provide said biopsy channel with a predetermined temperature for a predetermined period of time.

28. The method defined in claim 25, further comprising the step of:
   conducting electrical current through a conductor extending through said tubular member; and
   using said electrical current to at least partially sterilize said biopsy channel along said distal end portion of said elongate member.

* * * * *